United States Patent
List

(10) Patent No.: US 8,083,760 B2
(45) Date of Patent: Dec. 27, 2011

(54) LANCET SYSTEM WITH A STERILE PROTECTOR

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 254 days.

(21) Appl. No.: 11/941,951

(22) Filed: Nov. 18, 2007

(65) Prior Publication Data

US 2008/0125801 A1     May 29, 2008

Related U.S. Application Data

(63) Continuation of application No. PCT/EP2006/062387, filed on May 17, 2006.

(30) Foreign Application Priority Data

May 20, 2005    (EP) ..................................... 05011038

(51) Int. Cl.
     *A61B 17/32*      (2006.01)
(52) U.S. Cl. ........................................................ 606/181
(58) Field of Classification Search .................. 600/573, 600/578, 583, 584; 604/136, 130, 111, 192, 604/87–88; 606/181, 182, 183
See application file for complete search history.

(56) References Cited

U.S. PATENT DOCUMENTS

| | | | | |
|---|---|---|---|---|
| 5,267,972 A | * | 12/1993 | Anderson | 604/192 |
| 5,318,581 A | | 6/1994 | Sunmo | |
| 5,391,151 A | * | 2/1995 | Wilmot | 604/139 |
| 5,636,640 A | | 6/1997 | Staehlin | |
| 6,315,738 B1 | * | 11/2001 | Nishikawa et al. | 600/583 |
| 6,540,762 B1 | | 4/2003 | Bertling | |
| 2002/0052618 A1 | * | 5/2002 | Haar et al. | 606/181 |
| 2002/0120216 A1 | * | 8/2002 | Fritz et al. | 600/583 |
| 2002/0130042 A1 | * | 9/2002 | Moerman et al. | 204/403.01 |
| 2003/0050573 A1 | * | 3/2003 | Kuhr et al. | 600/567 |
| 2003/0153939 A1 | * | 8/2003 | Fritz et al. | 606/181 |
| 2003/0199893 A1 | * | 10/2003 | Boecker et al. | 606/181 |
| 2004/0034318 A1 | * | 2/2004 | Fritz et al. | 604/19 |
| 2004/0236248 A1 | * | 11/2004 | Svedman | 600/573 |
| 2005/0015020 A1 | * | 1/2005 | LeVaughn et al. | 600/583 |
| 2006/0008389 A1 | * | 1/2006 | Sacherer et al. | 422/102 |
| 2009/0030442 A1 | * | 1/2009 | Potter et al. | 606/182 |

FOREIGN PATENT DOCUMENTS

| | | |
|---|---|---|
| DE | 28 03 345 | 6/1979 |
| WO | WO 95/10977 | 4/1995 |
| WO | WO 01/66010 | 9/2001 |
| WO | WO 2004064636 A1 * | 8/2004 |
| WO | WO 2006082439 A1 * | 8/2006 |

* cited by examiner

*Primary Examiner* — Ryan Severson
*Assistant Examiner* — David Eastwood
(74) *Attorney, Agent, or Firm* — Bose McKinney & Evans LLP

(57) ABSTRACT

The present invention provides a lancet system having a lancet tip, a lancet body, and an outer body or housing which surrounds the lancet tip and in which the lancet tip is movable. The outer body or housing comprises deformable material which can be pierced by the lancet tip during a puncture operation to produce an outlet opening. The outlet opening can be widened during the puncture operation by a thickened or widened portion of the lancet body that at least partially protrudes through the opening. Other embodiments of the present invention include a pricking aid and/or lancet system provided as a magazine for holding a plurality of lancets.

30 Claims, 2 Drawing Sheets

LANCET SYSTEM WITH A STERILE PROTECTOR

RELATED APPLICATIONS

This application is a continuation application of International Application PCT/EP2006/062387, filed May 17, 2006, which claims priority to EP 05 011 038.6, filed May 20, 2005, which are hereby incorporated by reference in their entirety.

BACKGROUND

The present invention generally relates to a lancet system, and more particularly relates to a lancet system comprising at least one lancet having a lancet tip protected by a sterile protector.

The removal of body fluids such as blood is performed with the aim of subsequent analysis to diagnose illnesses or monitor the state of a patient's metabolism. Diabetics, in particular, remove samples of blood to determine the concentration of blood sugar. In order to remove only small amounts of blood, sharp, sterile lancets are quickly pierced into a patient's fingertip or other body part, for example, by hospital staff or by the patient himself. Lancet systems and other similar devices (for example, blood taking equipment, blood lancet devices, or pricking aids) which extract blood with minimal pain and in a reproducible manner are provided especially in the area of "home-monitoring," in which lay people carry out simple analyses of their blood.

Lancet tips used for blood extraction are typically sterilized in advance and are stored in a sterile state via a sterile protector (for example, in the form of a cap or pocket) before the lancet is used for a puncturing operation to prevent the tip from being contaminated by the surroundings. Furthermore, measures are frequently taken to ensure that, after a puncturing operation has taken place, the lancet tip is shielded or protected again (for example, by the same cap or pocket) to prevent injury and infections from blood that remains adhered to the lancet tip.

In the case of individual lancets, a sterile protector can be produced, for example, by encapsulating the lancet tip with plastic by injection molding both the lancet body and sterile protector during the same process. Before the lancet is used, the user manually removes the sterile protector upon inserting the lancet body into a pricking aid. In the case of lancets being encased in a magazine, similar sterile protectors are customary in which the lancet is pulled out of the sterile protector, whereby the sterile protector is moved out of the puncture path by a spring force. Relatively complicated mechanisms, such as springs, are integrated into the equipment to carry out this function.

Document WO 01/66010 discloses a lancet system that circumvents the complicated nature of this mechanism by piercing the sterile protector. In particular, document WO 01/66010 relates to a lancet comprising a lancet needle with a tip and a lancet body which completely surrounds the lancet needle at least in the region of the tip. In the region around the tip, the lancet body is composed of an elastic material in which the tip of the lancet needle is embedded. Furthermore, a lancet is disclosed having a lancet needle with a tip and a hollow body which surrounds at least the tip of the lancet needle. The lancet needle is movable in the region of its tip inside the hollow body, and the hollow body or housing is at least partially composed of an elastic material which can be punctured by the tip of the lancet needle during the puncturing operation. Further, and if appropriate, the hollow body or housing closes again after the tip of the lancet needle completes a puncturing operation and is retracted into the hollow body or housing.

Document DE 28 03 345 relates to equipment used for collecting blood samples that have a needle which can be applied to a patient's body part and an actuating device which has a ram and trigger for applying force to the needle in the direction of the needle tip. Blood lancets are used as needles and are individually disposed inside pockets of a strip package and are introduced into the equipment by a transporting device which acts on the strip package. The blood lancets are removed from the equipment after use, but while disposed inside the pockets, the ram of the actuating device drives the blood lancets. This equipment can either contain a cutting device by which the portion or region of the strip package closest to the needle tip can be severed before the application of force, or the blood lancets can perforate the strip package under the application of force.

U.S. Publication No. 2003/0199893 discloses a cutting device for cutting open a sterile barrier, but this requires substantial mechanical effort. The sterile barrier surrounds a penetrating element before a puncture operation and the barrier can either be opened by the cutting device or the penetrating element itself can penetrate through the sterile barrier.

In general, lancet systems should not be reused after having already performed a puncture operation. However, in home-monitoring environments, it is conceivable that a lancet system, once inserted into a pricking aid, will be used repeatedly by the same user before it is thrown away and replaced by a new lancet system. In a lancet system in which the sterile protector is pierced by the lancet itself to open the protector during a first puncture operation, after the first puncture operation, at least a portion of the sterile protector passes again in front of the lancet tip as the tip is retracted into the sterile protector. If a previously used lancet is reused, there is a risk that the used lancet will not pass through the originally created opening in the sterile protector, but rather will pierce a new opening in the sterile protector. In general, the lancet tip is not designed for piercing multiple openings, but rather for pricking skin with minimal pain. Upon each subsequent piercing of the sterile protector, which can be in the form of, for example, plastic material, the sharpness of the lancet tip begins to deteriorate. Further, after multiple puncture operations, parts of the sterile protector may detach from the sterile protector and possibly enter the pricking wound together with the lancet tip, which must be avoided.

Additionally, lancet systems known in the prior art are disadvantageous in that, during the retraction of the lancet tip through the outlet opening and into its original sterile protector, blood residues adhering to the lancet tip can scrape off at the edge of the outlet opening and adhere or attach to the outside of the sterile protector, thereby undesirably contaminating the surroundings.

SUMMARY OF THE INVENTION

Embodiments incorporating the present invention address the above-described disadvantages of the prior art and provide lancet systems or magazines in which at least a lancet tip is kept sterile in an unused state before it is used for the first time, and after it has been used, the lancet tip is stored in such a manner that the risk of contaminating the surroundings and unintentional injury sustained by the user is reduced.

In an exemplary embodiment, a lancet system comprises a lancet tip, a lancet body, and an outer body or housing which surrounds at least the lancet tip. The lancet tip is movable in the outer body or housing, which contains a plastic material that can be pierced by the lancet tip during a puncture operation to produce an outlet opening. The lancet body has a thickened or widened portion which is designed such that it widens or enlarges the outlet opening during the puncture operation, and the lancet tip is retracted into the outer body or housing after the puncture operation. In this embodiment, the lancet tip moves from a retracted position to an extended position during the puncture operation.

The lancet system has at least one lancet with a lancet tip. In another embodiment, the lancet system has multiple lancets. The lancet system can be a magazine for holding lancets that is inserted into a lancing aid or instrument.

When the lancet system is used correctly, the lancet tip pierces body tissue in order to cause body fluid, in particular blood or interstitial fluid, to flow out of the tissue. In one embodiment, the lancet tip may have, for example, a rotationally symmetrical design (for example, a conical or cylindrical shape). One or more polished sections may also be provided on the lancet tip. In a different embodiment, the edges of the tip can be inclined towards the longitudinal axis of the lancet tip and taper inwards toward the tip (for example, a blade-like cutting edge). Accordingly, this particular lancet tip has a sharp cutting edge and performs the puncturing operation in an advantageously less painful manner than is the case with rotationally symmetrical lancet tips.

The outer body or housing, which at least surrounds the lancet tip, maintains the lancet tip in a sterile condition. As a result, an unused lancet tip is shielded in a germproof manner, and therefore germs cannot contaminate the lancet tip until immediately before the lancet system is used. After being sterilized, the lancet tip remains sterile over an extended period of time.

The outer body or housing contains plastic material which can be pierced by the lancet tip during a puncture operation to produce an outlet opening. In this connection, "plastic" means that the material largely retains the shape given to it by an applied force. For example, the outlet opening in the outer body or housing, which is produced when the lancet tip pierces the plastic material, does not close after the lancet tip is retracted, as would be the case with elastic material. In the case of plastic material, the yield point is low relative to the break or fracture point of the material.

The plastic material can be provided, for example, as a film consisting of one material, or can be constructed in multiple layers from various plastic materials. During a puncture operation, the lancet tip of the lancet system pierces the plastic material and emerges from the outer body or housing through the outlet opening in order to prick the body tissue and remove body fluid.

The lancet body uses its thickened or widened portion, which is pushed through the outlet opening, to widen the outlet opening. In this connection, the thickened or widened portion is a region of the lancet body that has a larger diameter than the lancet tip and that can be moved through the outlet opening. This is advantageous because, after the puncture operation and when the lancet tip is retracted into the outer body or housing, the size of the outlet opening is maintained in the plastic material of the outer body or housing. Accordingly, the diameter of the outlet opening is larger than that of the lancet tip. The lancet tip, upon retracting into the outer body or housing, therefore does not scrape against or contact the edges of the outlet opening and thus does not contaminate the area at or near the outlet opening, which is positioned outside of the lancet system and situated beyond the reach of where body fluid residue adheres to the lancet tip. Furthermore, when emerging from the outlet opening in a subsequent puncture operation, the lancet tip does not strike or contact the plastic material again and therefore is not stressed by making an additional hole in the material, soiled by severed parts of the material, or contaminated by germs that adhere to the material. Advantageously, the risk of a used lancet tip contaminating the pricked wound produced during a previous puncture operation is reduced. After each puncture operation, the lancet tip is retracted into the outer body or housing and the user of the lancet system is protected from being unintentionally injured by the used lancet tip.

During the puncture operation, the lancet body may either be coupled to the lancet tip and moved jointly through the outlet opening and thereby widening the outlet opening after the lancet tip passes through, or the thickened or widened portion on the lancet body may be moved through the outlet opening independently of the lancet tip to widen the outlet opening after the tip passes through. In the former instance, there is an advantageously fixed spatial arrangement between the lancet tip and lancet body and, in the latter instance, the lancet body moves relative to the lancet tip.

In a different embodiment, the thickened or widened portion of the lancet body has a conical region (i.e., a conical shape), wherein the radius of the thickened or widened portion increases along the length of the lancet body away from the lancet tip. The conical region is advantageous because the outlet opening widens as the conical region is pushed through the outlet opening and this can be successively achieved by applying a lower force than, for example, if the lancet body had a bead-like thickened or widened portion.

In this embodiment of the lancet system, the thickened or widened portion is advantageously positioned adjacent to the lancet tip. As a result, the thickened or widened portion can widen the outlet opening almost instantaneously after the plastic material is pierced by the lancet tip.

The plastic material advantageously has a high elongation at tear (i.e., maximum elasticity), a low strength (i.e., transition from elastic to plastic behavior), a high modulus of elasticity, and a low indentation hardness. The elongation at tear of the plastic material is generally above 50% and the indentation hardness of the plastic material is generally below 50 $N/mm^2$. In particular, the plastic material is to be soft relative to the material of the lancet tip so that the latter is not damaged when it pierces the plastic material. For a lancet tip, for example, made of steel with a Vickers hardness of 250, the Vickers hardness of the plastic material should advantageously be below 25. In other embodiments, the plastic material can contain at least one material selected from the group consisting of LD (low density) polyethylene, HMW (high molecular weight) polyethylene, or polypropylene and, in particular, if the outer body or housing is integrally manufactured with the plastic material (for example, by injection molding). The plastic material typically contains at least one material selected from the group consisting of LD (low density) polyethylene, HMW (high molecular weight) polyethylene, polypropylene, aluminum, zinc, or polytetrafluoroethylene. This is especially the case if the outer body or housing is designed as a tubular hollow body and the plastic material is in the form of a film that closes an opening of the outer body or housing. If the film is manufactured from a metal, for example, it can additionally have a pressure-sensitive adhesive (e.g., in the form of a coating or layer of the film with hot-meltable polyethylene), which can be fastened or adhered to the outer body or housing.

In another embodiment, the lancet system contains a lancet needle which includes a tip and needle body, wherein the needle body is at least partially surrounded by a lancet body. In this embodiment, the lancet body may be fixedly connected to the needle body or the needle body may be movable relative to the lancet body (in order to carry out the puncturing operation). The lancet body may partially or completely surround the needle body. The lancet needle can be manufactured from a material which is sufficiently hard in order to withstand, without deformation, a mechanical stress applied to it during a puncturing operation, and in particular, when the plastic material is pierced, and/or during the processing steps or when subjected to any other stresses. Furthermore, the material has to be provided such that no particles break off or become detached from the lancet needle during the puncturing operation. That is, the plastic material can be torn or pierced, but should remain intact during the puncture operation. Finally, the lancet needle also has to be able to be processed in such a manner that the lancet tip can be polished to a sufficiently sharp point and the edges of the lancet tip can, if necessary, be polished to a sufficient degree of sharpness. Suitable materials for the lancet needle include various metals, and in particular specialty steels. However, needles made of ceramic or plastic are also possible.

The lancet body is movable relative to the outer body or housing, so that its thickened or widened portion, in order to widen the outlet opening produced by the lancet tip, can likewise be moved at least partially through the outlet opening.

In an advantageous embodiment, the outer body or housing completely surrounds the lancet body and the lancet tip such that the lancet body and the lancet tip are displaceable together in the hollow body or housing. In this embodiment, the lancet body and the lancet tip are advantageously displaceable in the longitudinal direction with respect to the lancet tip.

For the separate or joint movement of the lancet tip and lancet body, corresponding structural elements or mechanisms (for example, actuating means, drive unit, or securing elements) can be provided in a pricking aid in which the lancet system is used.

In one embodiment, the outer body or housing is designed as a tubular hollow body, wherein a first end is closed by a first film and a second end is closed by a second film and at least one of the two films comprises the plastic material. During a puncture operation with the lancet, and in particular during the initial puncture operation, the lancet tip pierces one of the films (which is composed of the plastic material) to produce an outlet opening through which the tip can emerge from the outer body or housing. In this embodiment, the first film can be opened by an actuating means or actuator which moves the lancet tip toward the second film and the second film comprises the plastic material and can be pierced by the lancet tip.

Furthermore, the outer body or housing may at least partially comprise a plastic body which is produced by encapsulating at least the lancet tip with the plastic material via injection molding. Furthermore, the outer body or housing may be composed entirely of the plastic material. A further possibility is the outer body or housing may be composed of the plastic material only in the area or region in which it is pierced by the lancet tip during the puncture operation. In this case, the regions which do not come into contact with the lancet tip may be manufactured from a different, perhaps more stiff, injection-moldable material.

Additionally, in another embodiment, a lancet system is designed as a magazine that holds a plurality of lancets. Each of the plurality of lancets has a lancet tip and is contained in an individual chamber of the lancet system. Each chamber has at least one chamber opening that is initially closed by a layer or film of plastic material, but the material can be pierced by the lancet tip during a puncture operation in order to produce an outlet opening. The lancet body has a thickened or widened portion which is designed to widen the outlet opening during the puncture operation. After the puncture operation, the lancet tip is retracted into the chamber.

The lancet system, when provided as a magazine, stores the unused and used lancets. The chambers of the magazine are functionally similar to the outer body or housing of the above-described lancet system. The chambers are advantageously arranged in a geometric configuration in the magazine, with it being possible for adjacent chambers to share common walls. The magazine may be constructed, for example, in the form of a stack, disk, or drum. The lancet tips are stored in their respective sterile protectors before they are used to maintain sterility. During a puncture operation, the lancet tip pierces the plastic material, which initially provides closure to the chamber opening in a germproof manner, and the thickened or widened portion of the lancet body widens the created outlet opening. After the puncture operation, the lancet tip is retracted into its chamber through the outlet opening to prevent unintentional injury from the lancet tip and/or to prevent contaminating the surroundings.

In a different embodiment, a pricking aid is provided which comprises at least one lancet system and an actuating means or actuator. The actuating means or actuator can act on the lancet system to move the lancet tip, for example, in the outer body or housing or the chamber, such that the lancet tip can pierce the plastic material and extend from the outlet opening to carry out a puncture operation. The lancet systems are inserted individually and manually into the pricking aid by the user. For example, multiple lancets, which are being held in a lancet system in the form of a magazine, can be inserted into the pricking aid. The actuating means or actuator (for example, a ram or hook) acts on an individual lancet so as to move the lancet tip to pierce the plastic material and carry out the puncture operation. Furthermore, the actuating means or actuator can retract the lancet tip into its outer body or housing or chamber after a puncture operation. However, an additional element (i.e., a spring) may also be provided in the pricking aid for this purpose. In addition, the actuating means or actuator may likewise move the thickened or widened portion of the lancet body through the outlet opening to further widen the outlet opening.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1C:
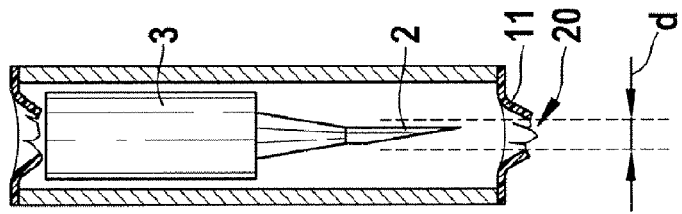
FIGS. 1a-c are schematic views in partial cross-section of a lancet system having a tip being moved in a puncture and retracting direction.
Figure 1B:
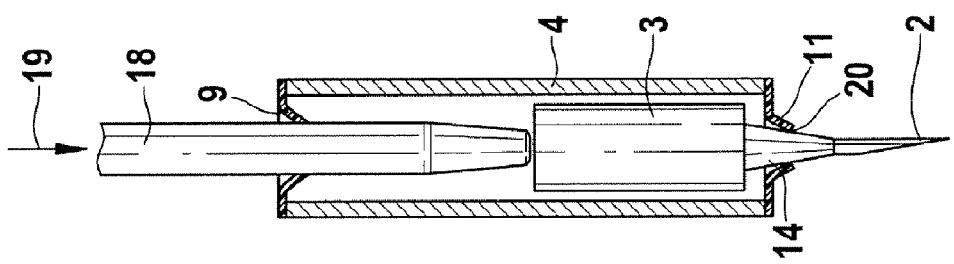
Figure 1A:
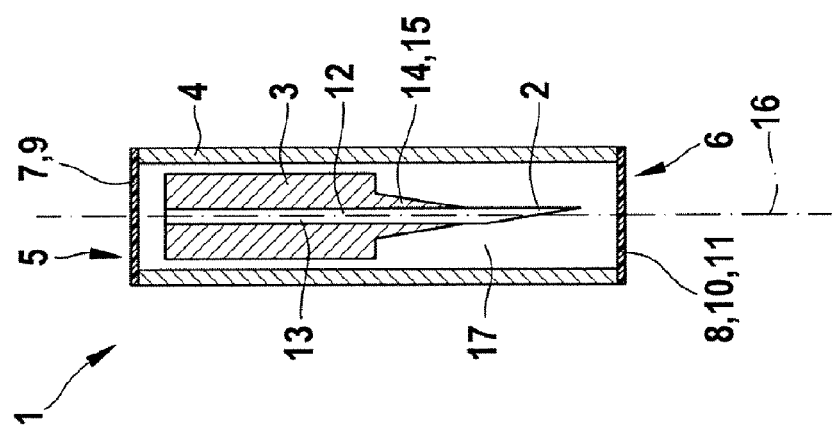
Figure 2:
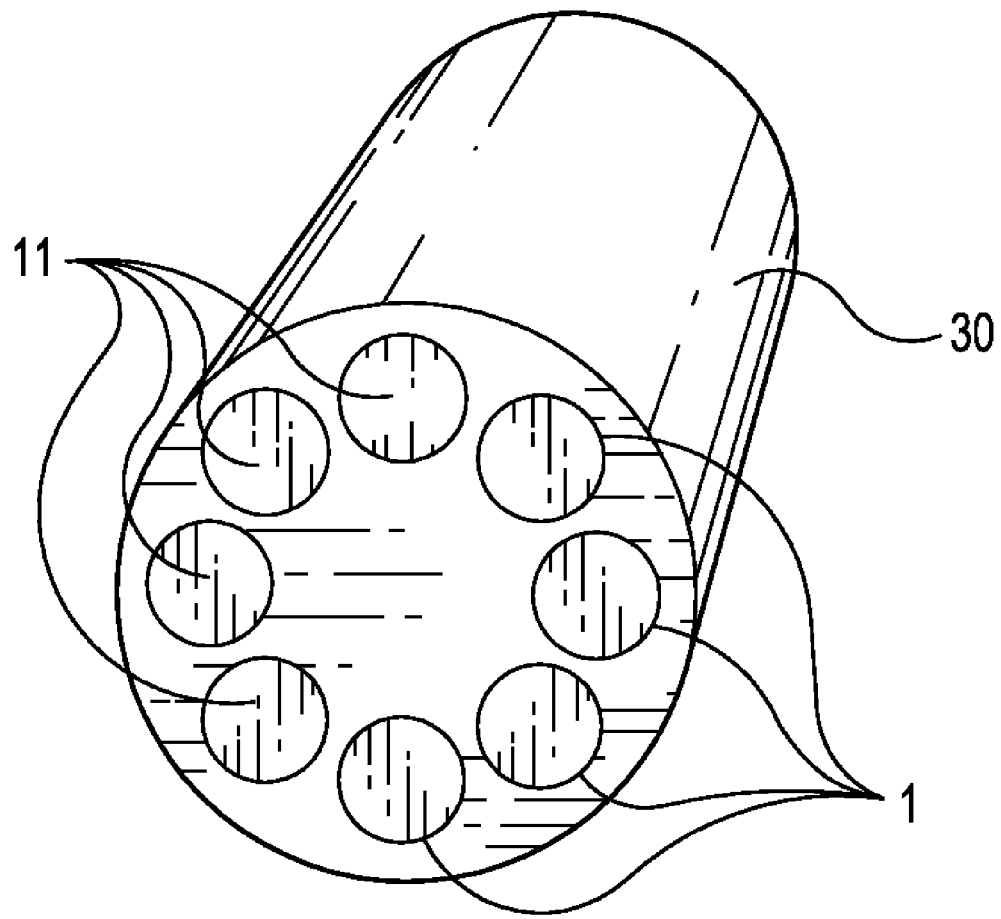
FIG. 2 is a perspective view of a lancet magazine 30 having a plurality of lancet systems 1 in chambers with each lancet system having a plastic member sealing its chamber.

FIG. 1 shows a lancet system 1 which has a lancet tip 2, a lancet body 3, and an outer body or housing 4. In FIG. 1a, the lancet system 1 is shown in partial cross-section along a line of symmetry 16 prior to being used. The outer body or housing 4 is designed as a tubular hollow body, with both ends 5, 6 of the outer body or housing 4 being closed in a germproof manner by two closures 7, 8. The two closures 7, 8 may be, for example, two films 9, 10, wherein at least the second closure 8 comprises plastic material 11.

The lancet system 1 contains a lancet needle 12 which comprises the lancet tip 2 and a needle body 13. The lancet body 3 surrounds the needle body 13 and has a thickened or widened portion 14 in the form of a conical region 15. The conical region 15 has a radius that increases along the length of the lancet body 3 in a direction away from the lancet tip 2. The thickened or widened portion 14 of the lancet body 3 is disposed adjacent to the lancet tip 2.

The outer body or housing 4 completely surrounds the lancet body 3 and the lancet tip 2, and the lancet body 3 and the lancet needle 12 (including lancet tip 2) are fixedly connected to each other. They can be moved together inside a cavity 17 of the outer body or housing 4.

In FIG. 1*b*, a puncture operation is being carried out using the lancet system 1 of FIG. 1*a*. An actuating means or actuator 18 exerts a force on the lancet body 3 and the lancet tip 2 in a puncture direction 19. To do so, the actuating means or actuator 18 pierces the first film 9 before entering the cavity 17 of the outer body or housing 4. The actuating means or actuator 18 then pushes the lancet tip 2 in the direction of the plastic material 11 such that the plastic material 11 is pierced by the lancet tip 2 and an outlet opening 20 is produced. While the lancet tip 2 continues to move in the pricking direction 19, the thickened or widened portion 14 is pushed in the puncture direction 19 through the outlet opening 20 and widens the opening due to its increasing cross-section.

In FIG. 1*c*, the lancet tip 2 is shown having been retracted into the cavity 17 of the outer body or housing 4 after the puncture operation. The retraction can be brought about, for example, by the actuating means or actuator 18 adhering or connecting to the lancet body 3 (for example, interlocks therewith) and pulling the lancet tip 2 in a direction opposite the pricking direction 19. The plastic material 11 now has a widened outlet opening 20 which remains widened due to the material properties of the plastic material. In this case, the diameter "d" of the outlet opening 20 has sufficient size such that the lancet tip 2 does not contact the plastic material 11 either during retraction into the outer body or housing 4 or during a subsequent puncture operation. Therefore, contaminating or applying additional stress to the lancet tip 2 by piercing through the plastic material 11 multiple times is avoided. Also, the risk of the lancet tip 2 or puncture wound being contaminated by the surroundings from body fluid residues which adhere to the lancet tip 2 after each puncture operation and that scrape off the tip and attach to the plastic material 11 is prevented.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS

1 Lancet system
2 Lancet tip
3 Lancet body
4 Outer body or housing
5 First end of the outer body or housing
6 Second end of the outer body or housing
7 First closure
8 Second closure
9 First film
10 Second film
11 Plastic material
12 Lancet needle
13 Needle body
14 Thickened or widened portion
15 Conical region
16 Line of symmetry
17 Cavity
18 Actuating means or Actuator
19 Puncture direction
20 Outlet opening

What is claimed is:

1. A lancet system for withdrawing body fluid from a body part, comprising:
   a housing;
   a lancet reciprocably disposed in the housing, the lancet comprising a first widening extending from a sharp lancet tip and at least one further widened portion, wherein the first widening and the further widened portion are separated by at least one section of a lancet shaft; and
   a plastic member sealing the housing;
   wherein, during a puncture movement of the lancet, the sharp lancet tip pierces the plastic member to produce an opening through which the sharp lancet tip then extends and punctures a body part, the further widened portion contacting the plastic member during the puncture movement and thereby enlarging the opening.

2. The lancet system of claim 1, wherein, after the puncture movement, the sharp lancet tip retracts into the housing, the opening in the plastic member substantially maintaining its shape after the retraction.

3. The lancet system of claim 1, wherein, during the puncture movement, the plastic member remains substantially intact.

4. The lancet system of claim 1, wherein, during the puncture movement, a portion of the plastic member pierced by the sharp lancet tip becomes flared.

5. The lancet system of claim 1, wherein the further widened portion comprises a substantially conical shape.

6. The lancet system of claim 5, wherein the radius of the further widened portion increases in a direction along the lancet away from the sharp lancet tip.

7. The lancet system of claim 1, wherein the radius of the first widening increases in a direction along the lancet away from the sharp lancet tip.

8. The lancet system of claim 1, wherein the plastic member comprises at least one material selected from the group consisting of polyethylene, polypropylene, aluminum, tin, and polytetrafluoroethylene.

9. The lancet system of claim 1, wherein the lancet defines a needle having the sharp lancet tip and the first widening, the needle being at least partially surrounded by a lancet body.

10. The lancet system of claim 1, wherein the housing comprises a first end and a second end, the first end including a first film and the second end including the plastic member.

11. The lancet system of claim 10, wherein the first film is configured to be pierced by an actuator and the lancet is adapted to be driven by the actuator during the puncture movement, thereby moving the sharp lancet tip toward the plastic member.

12. The lancet system of claim 1, wherein, during the puncture movement, the further widened portion enlarges the opening to a size that is substantially larger than the size of the first widening.

13. A lancet system for pricking a body part and withdrawing body fluid, comprising:
a magazine including a plurality of chambers;
a plurality of lancets, each one of the plurality of lancets being movably mounted in a respective one of the plurality of chambers, each lancet comprising a first widening extending from a sharp lancet tip and at least one further widened portion, wherein the first widening and the further widened portion are separated by at least one section of a lancet shaft;
a plurality of plastic members, each one of the plurality of plastic members sealing a respective one of the plurality of chambers; and
wherein, during a puncture movement of one of the plurality of lancets, the sharp lancet tip of the one lancet pierces the respective plastic member to produce an opening through which the sharp lancet tip then extends and punctures a body part, the further widened portion contacting the respective plastic member during the puncture movement and thereby enlarging the opening.

14. The lancet system of claim 13, wherein, during the puncture movement, the plastic member remains substantially intact.

15. The lancet system of claim 13, wherein, during the puncture movement, a portion of the plastic member pierced by the sharp lancet tip becomes flared.

16. The lancet system of claim 13, wherein the plastic member comprises at least one material selected from the group consisting of polyethylene, polypropylene, aluminum, tin, and polytetrafluoroethylene.

17. The lancet system of claim 13, wherein the further widened portion increases the size of the opening to be substantially greater than the size of the first widening.

18. The lancet system of claim 13, wherein each chamber comprises a first end and a second end, the first end including a first film and the second end including the plastic member.

19. The lancet system of claim 13, wherein, after the puncture movement, the sharp lancet tip retracts into the housing, wherein the opening in the plastic member substantially maintains its shape.

20. The lancet system of claim 19, wherein, after the sharp lancet tip retracts into the respective chamber, the size and shape of the opening remain substantially the same.

21. A lancet system, comprising:
a housing;
a lancet reciprocably disposed in the housing, the lancet comprising a first widening extending from a sharp lancet tip and at least one further widened portion, wherein the first widening and the further widened portion are separated by at least one section of a lancet shaft;
the lancet being movable between a retracted position and an extended position during a puncture movement;
wherein, in the retracted position of the lancet, a plastic member seals the housing and the sharp lancet tip is surrounded by the housing; and
further wherein, in the extended position of the lancet, the sharp lancet tip extends through an opening in the plastic member that is created when the sharp lancet tip pierces the plastic member during the puncture movement, the further widened portion contacting the plastic member and defining the size of the opening in the extended position.

22. The lancet system of claim 21, wherein the further widened portion comprises a substantially conical shape.

23. The lancet system of claim 22, wherein the radius of the further widened portion increases in a direction along the lancet away from the sharp lancet tip.

24. The lancet system of claim 21, wherein the plastic member comprises at least one material selected from the group consisting of polyethylene, polypropylene, aluminum, tin, and polytetrafluoroethylene.

25. The lancet system of claim 21, wherein, after the puncture movement, the lancet retracts into the housing from the extended position to the retracted position, wherein the opening in the plastic member substantially maintains its shape and size.

26. The lancet system of claim 25, wherein, as the lancet retracts to the retracted position, the lancet does not contact the plastic member.

27. The lancet system of claim 21, wherein, during the puncture movement, the plastic member remains substantially intact.

28. The lancet system of claim 21, wherein, during the puncture movement, a portion of the plastic member pierced by the sharp lancet tip becomes flared.

29. The lancet system of claim 21, wherein, in the extended position, the size of the opening is defined by the further widened portion in contact with the plastic member.

30. The lancet system of claim 21, wherein the further widened portion enlarges the opening to a size that is substantially larger than the size of the first widening.

* * * * *